United States Patent [19]

Odensten et al.

[11] Patent Number: 4,779,349
[45] Date of Patent: Oct. 25, 1988

[54] NOTCH MEASURING DEVICE

[76] Inventors: Magnus G. Odensten, Hjulsbrovägen 104, S-582 69 Linköping; Jan I. Gillquist, Stjärnorspsvägen Berg, S-590 61 Vreta Kloster, both of Sweden

[21] Appl. No.: 25,197

[22] Filed: Mar. 12, 1987

[30] Foreign Application Priority Data

Mar. 12, 1986 [SE] Sweden .................. 8601165

[51] Int. Cl.⁴ .................................. G01B 5/14
[52] U.S. Cl. ........................ 33/143 R; 33/169 R; 33/512; 33/147 K
[58] Field of Search ............ 33/169 R, 169 B, 143 R, 33/544, 512, 513, 511, 514, 147 K

[56] References Cited

U.S. PATENT DOCUMENTS

| | | | |
|---|---|---|---|
| 745,357 | 12/1903 | Lanham | 33/544 |
| 1,501,170 | 7/1924 | Korb | 33/169 B |
| 2,241,451 | 5/1941 | Fist . | |
| 3,274,692 | 9/1966 | Morrison | 33/169 B |
| 3,559,292 | 2/1971 | Weissman | 33/169 B |

FOREIGN PATENT DOCUMENTS

| | | | |
|---|---|---|---|
| 81636 | 9/1894 | Fed. Rep. of Germany | 33/3 A |
| 415971 | 7/1925 | Fed. Rep. of Germany . | |
| 0105901 | 6/1985 | Japan | 33/169 B |
| 4631 | of 1910 | United Kingdom | 33/143 R |
| 456576 | 11/1936 | United Kingdom | 33/178 R |

Primary Examiner—Harry N. Haroian
Attorney, Agent, or Firm—Banner, Birch, McKie & Beckett

[57] ABSTRACT

An instrument for measuring the distance between bone parts in a knee joint, particularly the distance between both femoral condyles (A', A") at the knee end of the femur (A), the instrument including a first element (3, 4, 12) with a first abutment surface (5), which is intended to be brought into engagement against one bone part (A'), and a second element (7, 9), which is displaceably mounted in the first element and at one end is provided with a second abutment surface (2) intended for being brought into engagement against the second bone part (A", C) there also being a scale (10) with an index for indicating the displacement of the second element in relation to the first element. The first element includes a tube (3, 4) bent at substantially a right angle, with the first abutment surface (5) situated on the outside of the bend. The second element (7, 9) is flexible (at 7), and inserted in the tube for displacement therein, so that the second abutment surface (2) projects out from the tube, the second element being provided at a distance from its first end with either the scale (10) or index, which can be read against the index or the scale of the first element.

4 Claims, 1 Drawing Sheet

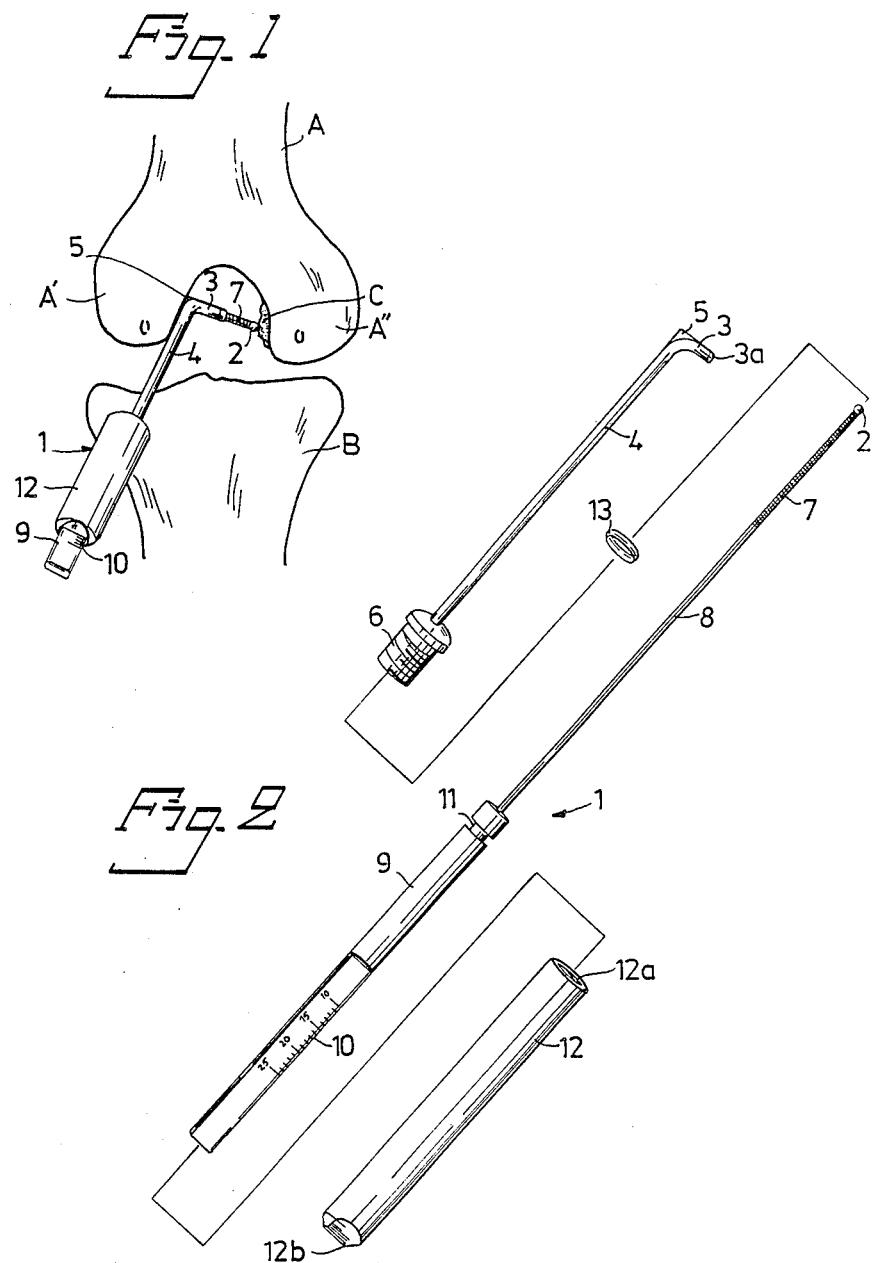

NOTCH MEASURING DEVICE

TECHNICAL FIELD

The present invention relates to a measuring instrument, more specifically to an instrument for measuring the distance between bone parts in a knee joint, in particular the distance between both femoral condyles at the distal end of the femur.

BACKGROUND ART

When a patient is suffering from injury to an anterior cruciate ligament which has not been surgically treated, the ligament disintegrates after a time, and at its attachment to the femur between both the femoral condyles thereof, a bony excrescence or osteophyte is formed. On remaking the joint, i.e. a surgical operation for fitting a new ligament, the osteophyte must first be removed with a chisel or the like, to recreate the normal space for the new ligament. The distance between the femoral condyles should normally be 21 mm, but may have decreased to about 11 mm due to the ostephyte.

To obtain the correct distance between the femoral condyles the distance must be measured continuously as the osteophyte is removed. So far, this has been done by using a forceps, which has been inserted between the femoral condyles so that the legs of the forceps have come into engagement against the inside of the respective condyle, after which the forceps has been removed while maintaining the distance between its legs, and this distance has been measured with the aid of a ruler.

Other devices that have been used for making the measurement are vernier calipers and angularly bent wires.

Accurate measurement cannot be made with the known devices. In addition, forceps and vernier calipers take up large space and require that a relatively large opening is made to the space inside the joint.

DISCLOSURE OF INVENTION

One object of the present invention is to at least mitigate the drawbacks with known measuring devices of the kind described in the introduction, and to provide an instrument which (a) gives a correct measurement, which can be read off directly at the measuring instant,
(b) takes up small space inside the knee joint,
(c) is operable at a sufficiently large distance from the knee joint itself, and
(d) has a simple and reliable implementation This object is achieved by an instrument in accordance with the invention having been given the distinguishing features disclosed in the characterizing portions of the claims.

BRIEF DESCRIPTION OF THE DRAWINGS

FIG. 1 is a perspective view of parts of a knee joint seen from the front with a measuring instrument in accordance with the invention inserted in the knee joint, and FIG. 2 is an exploded perspective view of the measuring instrument according to FIG. 1.

DETAILED DESCRIPTION OF THE PREFERRED EMBODIMENT

In FIG. 1 there are shown the parts of a knee joint on a right hand leg which include a femur A with two femoral condyles A' and A" and a Fibia or lower leg B. One of the two anterior cruciate ligaments (not shown), connecting the bones A and B has withered and an osteophyte C has formed at the attachment of this ligament at the condyle A".

Before a substitute ligament can be fitted into the knee, an opening is made in its anterior part for the insertion of a measuring instrument to measure the distance between the femoral condyles. Depending on how much the osteophyte C has grown, this distance is usually considerably less than the distance required for the substitute to be fitted and for it to function normally, and can be as little as 10-12 mm instead of the normal 20-22 mm. The osteophyte C must therefore be removed, which takes place by the surgeon inserting a chisel or the like through the mentioned opening in the knee and cutting away the osteophyte. Checking the distance between the condyles A' and A" takes place continuously with the aid of the measuring instruments until the normal distance is obtained.

In FIG. 1, a measuring instrument 1 in accordance with the invention is illustrated inserted in the opening in the knee joint for measuring the distance between the condyles A' and A". The instrument 1 comprises four components, all of which are illustrated in FIG. 2. The first component is a bent tube with a forward shorter tube part 3 forming a substantially right angle to a rearward longer tube part 4. The tube part 3 is somewhat shorter than the least distance generally present between the condyles A' and A" in the conditions in question, i.e. about 10 mm. The length of the tube part 3 is defined by the distance between the free opening 3a of the tube part and a projection 5 on the outside of the bend facing away from the centre of the bend. The portion of the projection 5 farthest from the opening 3a is in line with, or projects somewhat past the cylindrical surface of the tube part 4 farthest from the opening 3a. A threaded sleeve 6 is attached to the other end of the tube part 4.

The second component of the instrument comprises a forward, flexible part 7, which is attached to a steel rod having a central part 8 and a rear part 9. The part 7 has a length which exceeds by some cm the maximum normal distance between the condyles A' and A", and is illustrated in FIGS. 1 and 2 in the form of a helical spring with a ball 2 attached to its free end, although it may comprise a strip or wire of plastics or metal. The parts 7 and 8 have an outer cross section which is somewhat less than the suitably circular inner cross section of the tube 3, 4. The length of the part 8 is somewhat less than that of the tube part 4. The rear part 9 of the rod has a circular cross section, with the exception of a rear end portion, which has a substantially rectangular cross section and is provided with a scale 10 graduated in mm. The part 9 is also provided with an annular groove 11.

The third component of the instrument is a sleeve 12 with an inner cross section somewhat exceeding the cross section of the part 9. The sleeve 12 is provided with a forward, threaded opening 12a and a rear opening with a rectangular cross section somewhat greater than the rectangular cross section of the part 9. The sleeve 12 is somewhat shorter than the part 9.

The fourth component of the instrument is an elastic O ring 13, and is not entirely necessary, but has been provided to form a seal and/or a friction-increasing element between the sleeve 12 and the part 9.

In the assembled instrument 1 illustrated in FIG. 1, the parts 7 and 8 are inserted in the tube 3, 4, the rear end of the sleeve 6, engaging against the forward end of the part 9 when the parts 7, 8 have been thrust as far as possible into the tube 3, 4, a portion of the part 7 always being in the tube bend. The O ring 13 is inserted and retained in the groove 11. The part 9 is inserted in the sleeve 12 so that its rectangular section always projects out from the opening 12b. The sleeve 6 is threaded into the opening 12a of the sleeve 12 and tightened. The shoulder formed between the circular and rectangular sections of the portion 9 prevents withdrawal of the parts 7–9 backwards from the sleeve 12.

In use, the measuring instrument is inserted into the knee joint approximately in the way illustrated in FIG. 1, the user then having placed the projection 5 against one femoral condyle A' and has thrust the parts 7–9 forwards in the parts 3, 4, 6, 12 so that the ball 2 has come into engagement against the condyle A' or the osteophyte C. The movement of the parts 7–9 is brought about by the user gripping and retaining the sleeve 12 with one hand and gripping and displacing the portion of the part 9 projecting out from the sleeve 12 with the other hand, or alternatively with the little and third finger of the first hand. When the ball 2 is flushed with the opening 3a on the tube part 3, the sleeve opening 12a, with its outwardly facing and surface serving as index, is situated directly opposite a mark on the scale 10 corresponding to the length of the tube portion 3 between the projection 5 and opening 3a, in this case a mark with the notation 10 mm. For each mm by which the ball projects out of the opening 3a there is a corresponding displacement of one mm of the scale 10 in relation to the index 12b, there being a mark on the scale for every mm and a longer mark for each fifth mm, the longer mark being provided with a numerical denotation.

The distance between the femoral condyles A' and A" can thus be read directly on the scale 10 without the instrument 1 needing to be removed from the knee joint. So that the reading will not be changed by an unintentional displacement of the parts 7–9 in relation to the parts 3, 4, 12, there should be a certain amount of friction between them, which may be achieved by a rough outer surface on the flexible portion 7 and/or by the O ring 13, which resiliently engages against the inside of the sleeve 12.

Different modifications and embodiments of the measuring instrument described above and illustrated on the FIGURES are possible of course, without departing from the inventive concept. The invention is thus only restricted by the disclosures in the claims.

We claim:

1. Instrument for use in measuring the distance between the femoral condyles (A',A") at the end of the femur (A) in a knee joint, said instrument comprising a first element (3, 4, 6, 12) and a second element (7–9), said first element comprising a sleeve (12) and a tube (3, 4) extending axially from said sleeve, said tube (3,4) being bent at substantially a right angle to provide a linear tube end (3) that is shorter than the distance between the condyles (A', A"), a first abutment surface (5) disposed at the outside of the bend opposite from the free end of said linear tube end (3) for bringing one condyle (A') into contact therewith when said linear tube end is disposed between said condyles (A', A"), said second element (7–9) comprising a rod (8) including a flexible end (7) inserted in said tube (3, 4) for endwise movement relative thereto with said flexible end (7) for movement through the bend in said tube (3, 4) and having a free end emerging from said linear tube end (3) to provide a second abutment surface (2) for engaging the second condyle (A", C), said rod including a base portion (9) diametrically enlarged relative to said rod and received and moveable endwise within said sleeve (12) with the end thereof opposite from said rod defining a free end extending from said sleeve, O-ring friction enhancing means disposed between said base portion (9) of said second element (7–9) and said sleeve (12) of said first element (3–6, 12), and said base portion (9) and said sleeve (12) having cooperating scale means (10) and index means (12b) for indicating the relative position of said first element endwise within said second element and the distance between said femoral condyles, said sleeve serving as a handle for positioning the tube end (3) between the condyles (A', A") with the first abutment surface (5) in engagement with the one condyle (A') and the free end of said base portion (9), said handle being graspable for moving said second element endwise of said first element and thereby moving said second abutment surface into engagement with the second condyle (A"), with the position of said second abutment surface relative to the free end of said tube end (3) and the distance between femoral condyles being readable at said scale and index.

2. Instrument in accordance with claim 1 in which said sleeve (12) is removably attached at one end to said tube (3, 4).

3. Instrument in accordance with claim 2 in which the end of said sleeve (12) opposite from the end attached to said tube (3, 4) is provided with an opening (12b) through which the base portion (9) of the second element (7–9) projects, said scale being formed on the projecting end portion of said base portion (9) and the end of said sleeve about said opening (12b) defining said index.

4. Instrument in accordance with claim 2 in which said tube end (3) has a maximum length from said first abutment surface (5) to the free end (3a) thereof of about 20 mm, preferably about 10 mm.

* * * * *